(12) United States Patent
Giampapa et al.

(10) Patent No.: US 9,968,546 B2
(45) Date of Patent: *May 15, 2018

(54) TOPICAL COMPOSITION FOR SKIN TREATMENT TO REDUCE LINES AND WRINKLES OF THE FACE AND BODY USING A DUAL DNA REPAIR MECHANISM TO ADDRESS DAMAGE CAUSED BY AGING AND ULTRA-VIOLET INDUCED DAMAGE TO THE SKIN WITH COMBINATION OF SKIN TURGOR ENHANCEMENT COMPOUNDS

(71) Applicants: Vincent C Giampapa, Montclair, NJ (US); Kellie Serrault, Fort Worth, TX (US); Gregory Serrault, Fort Worth, TX (US)

(72) Inventors: Vincent C Giampapa, Montclair, NJ (US); Kellie Serrault, Fort Worth, TX (US); Gregory Serrault, Fort Worth, TX (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/347,022

(22) Filed: Nov. 9, 2016

(65) Prior Publication Data

US 2017/0128355 A1 May 11, 2017

Related U.S. Application Data

(60) Provisional application No. 62/253,530, filed on Nov. 10, 2015.

(51) Int. Cl.
| A61K 9/127 | (2006.01) |
| A61K 8/97 | (2017.01) |
| A61Q 19/02 | (2006.01) |
| A61Q 19/08 | (2006.01) |
| A61K 8/49 | (2006.01) |
| A61K 8/41 | (2006.01) |
| A61K 8/67 | (2006.01) |
| A61K 8/46 | (2006.01) |
| A61K 8/63 | (2006.01) |
| A61K 8/34 | (2006.01) |
| A61K 8/31 | (2006.01) |
| A61K 8/35 | (2006.01) |
| A61K 8/14 | (2006.01) |
| A61K 8/25 | (2006.01) |
| A61K 8/26 | (2006.01) |
| A61K 8/42 | (2006.01) |

(52) U.S. Cl.
CPC ............ *A61K 8/97* (2013.01); *A61K 8/14* (2013.01); *A61K 8/25* (2013.01); *A61K 8/26* (2013.01); *A61K 8/31* (2013.01); *A61K 8/34* (2013.01); *A61K 8/342* (2013.01); *A61K 8/345* (2013.01); *A61K 8/355* (2013.01); *A61K 8/41* (2013.01); *A61K 8/42* (2013.01); *A61K 8/46* (2013.01); *A61K 8/4986* (2013.01); *A61K 8/63* (2013.01); *A61K 8/676* (2013.01); *A61K 8/678* (2013.01); *A61Q 19/02* (2013.01); *A61Q 19/08* (2013.01); *A61K 2800/524* (2013.01)

(58) Field of Classification Search
CPC ...... A61K 2800/524; A61K 8/14; A61K 8/25; A61K 8/26; A61K 8/31; A61K 8/34; A61K 8/342; A61K 8/345; A61K 8/355; A61K 8/41; A61K 8/42; A61K 8/46; A61K 8/4986; A61K 8/63; A61K 8/676; A61K 8/678; A61K 8/97; A61K 8/88; A61K 8/898; A61Q 7/00; A61Q 19/10; A61Q 1/02; A61Q 1/04; A61Q 1/06; A61Q 1/08; A61Q 1/10; A61Q 1/12; A61Q 5/00; A61Q 5/002; A61Q 5/006; A61Q 5/04; A61Q 5/06; A61Q 5/10; A61Q 5/12

See application file for complete search history.

(56) References Cited

U.S. PATENT DOCUMENTS 8,911,774 B2    12/2014 Giampapa
2005/0226825 A1  10/2005 Giampapa

*Primary Examiner* — Nannette Holloman
(74) *Attorney, Agent, or Firm* — Melvin K. Silverman

(57) ABSTRACT

A topical composition for anti-aging and anti-UV damage treatment of the skin includes water soluble extract of *Uncaria* species, *Arabidopsis thaliana* extract, alpha lipoic acid, dimethylethanolamine, tetrahexyldecyl ascorbate, dimethyl sulfoxide, *Glycyrrhiza Glabra* (licorice) root extract, methylsulfonylmethane, phytosterols, D-ribose, tocotrienol, tocopherol, glucosamine hydrochloride, *Pisum sativum* extract; silicates of sodium, magnesium and aluminum, and a dermatologically acceptable liposomal delivery medium. The composition is useful in a method using it for anti-aging skin treatment effecting DNA repair in both the nucleus and the mitochondria. The topical composition can be applied on the skin of a person daily, and can also be applied in a dermal infusion treatment, with or without micro-dermal abrasion or skin suction. Topical application of the composition achieves effective reduction of pigmentation spots, degree of winkles, and improvement of skin color, tone and turgidity, particularly of the eyelid and facial areas.

10 Claims, 3 Drawing Sheets

BEFORE

AFTER

BEFORE

AFTER

BEFORE

AFTER

TOPICAL COMPOSITION FOR SKIN TREATMENT TO REDUCE LINES AND WRINKLES OF THE FACE AND BODY USING A DUAL DNA REPAIR MECHANISM TO ADDRESS DAMAGE CAUSED BY AGING AND ULTRA-VIOLET INDUCED DAMAGE TO THE SKIN WITH COMBINATION OF SKIN TURGOR ENHANCEMENT COMPOUNDS

FIELD OF THE INVENTION

This invention relates to a topical composition for anti-aging skin treatment and a method of anti-aging skin treatment utilizing dual actions of DNA repair in the nucleus and the mitochondria to repair oxidative and non-oxidative DNA damages and a combination of other ingredients that cause the skin to look younger, and remove eyelid bulges and fine lines of the face and body.

BACKGROUND OF THE INVENTION

This application reflects an improvement of the invention of U.S. Pat. No. 8,911,774 of Vincent Giampapa, one of the inventors herein. Such improvement provided enhanced suppleness to the skin, anti-aging benefits and repair of UV-related damage.

Aging is the accumulation of random damage to the building blocks of life, especially to DNA, certain proteins, carbohydrates and lipids, which begins early in life and eventually exceeds the body's self repair capabilities.

Photoaging is the complex of damages that accumulate from life-long exposure to solar ultraviolet light (UV-A and UV-B). It produces wrinkling, loss of elasticity, erythema, hyperpigmentation, and increased risk of skin cancer. UV radiation acts on the epidermis through direct exposure, and on the underlying dermis through cell-to-cell molecular signaling. Collagen fibrils in the extracellular matrix of the dermis are responsible for the strength and resiliency of the skin. Wrinkling occurs due to the loss and scarring of the dermal collagen fibrils that results from chronic exposure to solar UV.

UV irradiation leads to elevated levels of matrix metalloproteinases in human skin (MMPs). One of these enzymes, MMP-1 (also known as collagenase-1), cleaves collagen type 1, the primary constituent of the collagen fibrils in the extracellular matrix of the dermis. The imbalance of MMP-1 promotes the scarring of the collagen fibril structures. The resultant disorganization of collagen fibrils in the dermal connective tissue leads to loss of skin tone and wrinkling.

UV-A radiation has been shown to penetrate the under layers of the skin, and produce oxidative DNA damage. Following exposure of the skin to ultraviolet radiation free radicals are generated, which frequently trigger the release of inflammatory mediators. Among the inflammatory chain activities triggered by free radicals, it is known that the transcription factors NF-kB and activator protein 1 (AP-1) are activated by free radicals and pro-inflammatory cytokines, which are generated by free radical activity.

The UV-induced DNA damage also activates immunosuppressive pathways that inhibit the cutaneous immune system from reacting to challenges from the environment and tumors. The immunosuppressive cytokines TNF-Alpha and IL-10 have been observed among the repertoire of cellular responses following UV irradiation.

Irradiation by UV-A also acts to damage DNA indirectly, through the formation of oxygen radicals, to oxidize guanine to 8-oxo-guanine in nuclear and mitochondrial DNA. The oxidative events of UV-A irradiation, including metabolic stress associated with loss of mitochondrial DNA, also are associated with the inflammatory responses that lead to the release of collagen-degrading metalloproteinases into the dermal layer.

UV-B radiation, commonly referred to as the sunburn rays, is the one that cause the most concern. At the molecular lever, it is known that UV-B irradiation produces non-oxidative DNA damage, which results in DNA structural changes through dimer formation. More specifically, UV-B irradiation causes DNA damage in skin by linking adjacent bases to form cyclobutane purimidine dimer (CPD). These may be of the thymine-thymine type, or they may be between adjacent cytosines, or other combinations. CPDs are slowly removed from the DNA by a natural excision repair process, which removes about 50% of the CPDs in 24 hours. Furthermore, it is believed that a combination of UV-A and UV-B damages may be the formation of CC-TT dimer tandem doubles. These tandems may occur on the p53 tumor suppressor gene and may lead to the formation of squamous cell carcinomas. The non-oxidative DNA alteration damage is commonly assessed by quantifying the formation of TT dimers within the cells. By utilizing human living epidermal cell equivalents HaCaT Keratinocytes the amount of cyclobutyl pyrimidine TT dimers (CPD) formed can be measured.

As can be appreciated, danger occurs when DNA is damaged but not severely enough to stimulate apoptosis (natural cell death), the damaged cells then reproduce the unrepaired DNA, which initiates a continuum. The skin loses moisture and becomes dull, dry, and rough without tone and texture. Blotches, hyperpigmentation, fine lines and wrinkles develop and, then, premalignant actinic keratoses form. Finally these age spots may become malignant squamous cell carcinomas.

Various pharmaceutical or cosmetic products have been developed for treating age spots resulted from chronic UV light exposure. Most products treat age spots by bleaching, and topical color reduction by chemical reactions, however, they do not repair DNA damages, or prevent re-occurrence of skin pigmentation. On the other hand, many skin care products now include antioxidants to reduce free radicals and address oxidative damages.

Recently, *Arabidopsis thaliana* extract containing active component of oxoguanine glycosylase-1 has been used with liposome for restoring the DNA damaged by oxidative stress in the nucleus and in the mitochondria. However, the function of oxoguanine glycosylase-1 does not address non-oxidative DNA damages caused by UV-B.

U.S. Patent Application Publication No. 20050226825 A1 discloses a topical composition containing water soluble extract of *Uncaria* species for repairing DNA damages caused by UV-B radiation by reducing dimer formation.

As can be appreciated, existing topical skin care products have limited functions in preventing and repairing DNA damages, therefore, have limited effects in preventing and restoring age related deterioration of skin conditions, particularly damage of skin about the eyes, Therefore, it is desirable to have a topical composition that addresses multiple major causes of skin aging, particularly, photoaging caused by both oxidative and non-oxidative DNA damages, and inflammatory response caused by oxidative stress.

SUMMARY OF THE INVENTION

In one embodiment, the present invention is directed to a topical composition for anti-aging skin treatment. The topical composition includes water soluble extract of *Uncaria* species, *Arabidopsis thaliana* extract, lipoic acid, dimethylethanolamine, tetrahexyldecyl ascorbate, dimethyl sulfoxide, *Glycyrrhiza Glabra* (licorice) root extract, methylsulfonylmethane, phytosterols, d-ribose, tocotrienol, tocopherol, glucosamine hydrochloride, *Pisum sativum* extract, silicates of sodium, magnesium and aluminum, and acetyl hexapeptide 8 within a dermatologically acceptable liposomal delivery medium. To this composition may be added *Bambusa vulgaris* extract which is a form of bamboo silica.

In another embodiment, the present invention is directed a method of anti-aging skin treatment that comprises topically applying the topical composition on one or more areas of the skin of a person, which results in reduction of pigmentation spots and degree of winkles, and improvement of skin color tone. The topical composition can be topically applied on the areas of interest one or more times daily. Moreover, the topical composition can also be applied by dermal infusion treatment.

In a further embodiment, the instant invention is directed to a composition providing increased turgidity and suppleness to the skin.

Further advantages of the invention will become apparent from the following description showing exemplary embodiments of the invention.

DETAILED DESCRIPTION OF THE INVENTION

Figure 1:
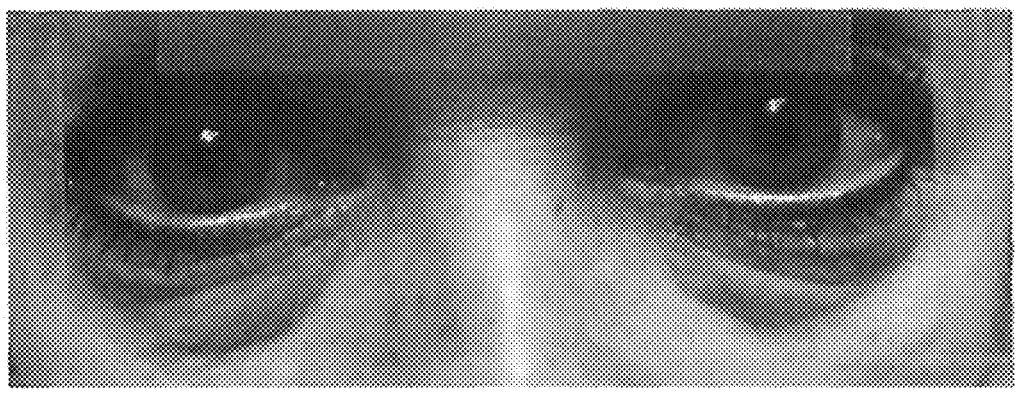
FIGS. 1, 3 and 5 are photographs of three subjects before use of the inventive composition.

In one embodiment, the present invention provides a topical composition for anti-aging skin treatment using dual DNA repair mechanism. The topical composition comprises a plurality of active components with different functionalities, including antioxidants, DNA repair components, antiglycation components, anti-inflammatory components, cellular hydration components, age spot reduction components, and collagen stimulating components in a dermatological acceptable liposomal delivery medium.

Unless defined otherwise, all technical and scientific terms used herein have the same meaning as commonly understood by one having ordinary skills in the art to which the invention pertains.

It should also be understood that various chemicals used herein may have more than one type of properties described herein. Therefore they may be listed or described in more than one of the categories of the active components. For example, tocopherol acetate is a strong antioxidant, and it also increases collagen synthesis, as such, it is also a collagen stimulating component.

Antioxidants inhibit free radical productions. Decrease in free radical levels promotes repairing of damaged cell membranes as well as cellular hormonal receptors. Antioxidants also help to inhibit AP-1, which is the key compound noted to be involved in skin aging and collagen breakdown. Research has shown that lower DNA damage levels also correlate with lower free radical levels. The examples of suitable antioxidants include, but are not limited to, alpha lipoic acid, tocotrienol, tocopherol, tetrahexyldecyl ascorbate, dimethyl sulfoxide, and retinyl palmitate.

Alpha lipoic acid is an extremely potent anti-oxidant that is both water and fat-soluble. Alpha lipoic acid is used in the topical composition in a concentration range from about 1% to about 5% by weight (w/w).

Tetrahexyldecyl ascorbate is a stable, oil soluble form of Vitamin C. It is very soluble in ethanol, hydrocarbons, esters and vegetable oils. It has been found that tetrahexyldecyl ascorbate penetrates the skin four times better than magnesium ascorbyl phosphate, delivers pure Vitamin C fifty times better than ascorbic acid. It has been reported that tetrahexyldecyl ascorbate inhibits MMP-2 and MMP-9 over three times better than ascorbic acid, decreases 8-OHdG induced by UV-A radiation, decreases p53 expression induced by UV-B radiation, and increases collagen synthesis at least twice as much as ascorbic acid. It has also been reported that at a concentration of 0.1% tetrahexyldecyl ascorbate reduces melanin synthesis by 80%. It is believed that tetrahexyldecyl ascorbate protects the cells against UV-B radiation better than other esters of Vitamin C. On the other hand, in Korea tetrahexyldecyl ascorbate is approved as a functional ingredient for whitening at 2%. Therefore, as can be appreciated, tetrahexyldecyl ascorbate is a multi-functional component. It is effective in anti-oxidation, collagen synthesis and protection, whitening, MMP inhibition, and DNA protection. The concentration of tetrahexyldecyl ascorbate in the topical composition is in a range from about 0.5% to about 2% (w/w).

Retinyl palmitate, or vitamin A palmitate, is a common vitamin supplement for oral administration, and it has also been used in skin care products. Retinyl palmitate is used as an antioxidant. After its absorption into the skin, retinyl palmitate is converted to retinol, and ultimately to retinoic acid (the active form of Vitamin A).

Dimethyl sulfoxide (DMSO) is a potent anti-oxidant and an anti-inflammatory agent. Dimethyl sulfoxide dissolves both polar and nonpolar compounds and is miscible in a wide range of organic solvents as well as water. More importantly, it has a distinctive property of penetrating the skin very readily, and it has the ability to carry other substances through membranes. Therefore, in addition to its antioxidant and anti-inflammatory properties, dimethyl sulfoxide is also used as a delivery agent in the instant topical composition. The concentration of dimethyl sulfoxide is in a range from about 0.5% to about 2% (w/w).

As an important feature of the present invention, the topical composition comprises DNA repair components of natural ingredients. Two distinct compounds, namely water soluble extract of *Uncaria* species and *Arabidopsis thaliana* extract, are utilized to repair both mitochondrial and nuclear DNAs.

The *Uncaria* species herein includes *tomentosa, guianensis, pteropoda, homomalla, perrottetii,* or *rhynchopylla*. Preferably, *Uncaria tomentosa* is used in the topical composition. Water soluble extract of an *Uncaria* species can be obtained using hot water, cold water or alcohol extraction of the *Uncaria* species using methods known in the art. Hot water extraction of *Uncaria* species has been known and used for hundreds of years as a natural herbal treatment. Native Indians prepare treatments of *Uncaria* by drinking hot water extracts as a tea. Recently, U.S. Pat. Nos. 6,361,805, 6,238,675, 6,039,949, and 6,964,784, which are hereby incorporated by reference in their entirety, each teach a particular hot water extraction method. The method produces a hot water extract from the bark of *Uncaria tomentosa*, where the fraction of the extract having a molecular weight less than 10,000 is separated as the extract product. This product is in a form of beige to brown-orange hygroscopic fine powder, and it contains no less than 16% of carboxy alkyl esters and it is readily soluble in water (solubility in water >400 mg/ml). The water soluble extract of an *Uncaria* species is commercially available from various sources, for example, from Phoenix Lab. Inc. (Hicksville, N.Y.) and Raintree Nutrition, Inc. (Carson City, Nev.).

NF-kB is known to control the nuclear events that salvage cells from apoptotic cell death and pro-inflammatory cytokine production (Beg, et al., An essential role for NF-kB in preventing TNF-.alpha. induced cell death Science 274: 782-784, 1996; Wang et al., TNF-.alpha. and Cancer Therapy-induced Apoptosis: Potentiation by Inhibition of NF-KB. Science 274: 784-787, 1996). It has been reported that the water soluble extract of the *Uncaria* species effectively induces apoptosis in HL-60 leukemic cells in vitro, as a result of NF-kB inhibition, hence, it possesses anti-tumor, anti-inflammatory and immune stimulating properties. Moreover, it has been reported that the water soluble extract of the *Uncaria* species enhances DNA repair in both rats and humans, wherein the DNA repair process removes DNA damages in the nucleus, which inhibits cell replication and immune function (see U.S. Pat. No. 6,039,949). Water soluble extract of the *Uncaria* species has been used orally as a supplement for inhibiting inflammatory response and treating disorders associated with inflammatory response by inhibiting TNF-.alpha. production or induce apoptosis of white blood cells.

Most recently, as disclosed in U.S. Patent Application Publication No. 20050226825 A1, which is hereby incorporated by reference in its entirety, it has been found in-vitro study that after UV-B exposure, human HaCaT (keratinocyte line) cells incubated with a solution of water soluble extract of the *Uncaria* species have substantially less cyclobutane purimidine dimer (CPD) formation in the nucleus in comparison to untreated cells. Therefore, the water soluble extract of the *Uncaria* species improves skin cell's resistance to DNA damage and enhances DNA repair capacity by reducing formation of CPDs.

Water soluble extract of the *Uncaria* species is used in the topical composition of the present invention for repairing non-oxidative DNA damages by reducing CPD formation, and as an anti-inflammatory agent utilizing its NF-kB and TNF-.alpha. inhibition properties. It has been found that when water soluble extract of *Uncaria tomentosa* is used, its concentration in the topical composition can be in a range from about 0.5% to about 5% (w/w), preferably from about 0.75% to about 3% (w/w).

On the other hand, oxidative stress damages the membrane of cells and the DNA of the nucleus and mitochondria. Oxidation happens with normal metabolism and UV-A radiation. It has been reported that 10,000 bases per cell are damaged every day. Oxidative DNA damages cause formation of 8-oxo-guanine in mitochondria and an increase in MMP-1 release. Mitochondria have about 1-2% of the total DNA. However, this circular DNA is important because mitochondrial DNA codes for sub-units of ATP synthase, NADH dehydrogenase, cytochrome oxidase, and other proteins.

Traditionally, oxidative damages are addressed by using antioxidants in skin care products. It is important to understand that antioxidants can only protect DNA by reducing free radical formation, however, antioxidants cannot repair DNA after it has been excessively damaged.

Oxoguanine glycosylase-1 (OGG1) is a DNA repair enzyme that excises 8-oxo-guanine (8 oG). This enzyme has 424 amino acids and a molecular weight of 47 kD in its precursor form in humans. It has been reported that oxoguanine glycosylase-1 excises the damaged base and acts with an associated lyase activity for chain cleavage. Oxoguanine glycosylase-1 can be trapped by mitochondrial membranes, and increased levels of oxoguanine glycosylase-1 are found in the mitochondria of aged livers, indicating that the import of oxoguanine glycosylase-1 needed for DNA repair in mitochondria declines with age.

Oxoguanine glycosylase-1 is found in the plant *Arabidopsis thaliana*. The extract of *Arabidopsis thaliana* is commercially available. It has been found that oxoguanine glycosylase-1 encapsulated in liposome can penetrate mitochondria and repairs mitochondrial DNA effectively. Commercially, oxoguanine glycosylase-1 in liposome is provided by AGI Dermatics, (Freeport, N.Y.) under the trade name of Roxisomes™. It has been reported that in-vitro study treatment of keratinocytes with 0.5% Roxisomes™ reduces the amount of damage to the mitochondria from peroxide by approximately 30% and also prevents further damage over time.

In one embodiment, *Arabidopsis thaliana* extract is used in the topical composition for restoring the DNA damaged by oxidative stress in the mitochondria and in the nucleus. The concentration of *Arabidopsis thaliana* extract is in a range from about 0.5% to about 2% (w/w).

As can be appreciated, the unique combination of water soluble extract of the *Uncaria* species and *Arabidopsis thaliana* extract in the topical composition of the present invention provides dual actions of DNA repair. The former mainly repairs DNA in the nucleus and the latter mainly repairs DNA in the mitochondria, hence the dual actions of the topical composition are also referred to as a dual DNA repair mechanism. Furthermore, the dual DNA repair actions address DNA damages caused by both oxidative and non-oxidative damages. Moreover, the anti-inflammatory property of the water soluble extract of the *Uncaria* species further broadens the spectrum of the protective actions. Therefore, this synergetic and unique combination provides strong advantages over existing anti-aging skin care technologies, which typically focus on only one aspect of the causes, or one type of repairing actions. Furthermore, the topical composition of the present invention addresses DNA damages caused by both intrinsic (metabolic and natural aging) and extrinsic (UV radiations) reasons. As can be appreciated, enhancing DNA repair in both the nucleus and the mitochondria ultimately reduces CPD formation, which reduces the cause of skin cancer.

In addition to the components enabling DNA repair, the topic composition further comprises D-ribose as an essential material for the DNA repairing process. D-ribose is a pentose present in all living organisms. It is an essential element of the structure of the ATP molecule, and is directly involved in ATP synthesis. It has also been reported that D-ribose in a cosmetic composition improves cellular respiration and intracellular ATP production, and it improves metabolism of the cutaneous cells and tissues. The concentration of D-ribose is in a range from about 0.01% to about 0.05% (w/w).

In a further combination with several potent antioxidants described above, the topical composition of the present invention effectively reduces DNA damages by reducing the cause of oxidative damage, and by effectively repairing the DNA as damage occurs.

As described above, the water soluble extract of the *Uncaria* species is an anti-inflammatory agent. Alpha lipoic acid is also a strong anti-inflammatory agent. These compounds inhibit NF-KB and TNF-.alpha., which are pro-inflammatory compounds activated by UV-A and UV-B sunlight. The inhibition of NF-KB and TNF-.alpha. in skin cells helps to keep collagen and elastin from breaking down, caused by metaloprotease and collagenases.

It is known that glycation of collagen increases uniformly with age, leading to a uniform increase in the glycation-product content of the skin, which accelerates skin wrinkle formation. These glycation products include, for example, pyrraline, carboxymethyl-lysine, pentosidine, crosslines, Ne-(2-carboxyethyl)lysine (CEL), glyoxal-lysine dimer (GOLD), methylglyoxal-lysine dimer (MOLD), 3DG-ARG imidazolone, versperlysines A, B, C, threosidine or, alternatively, advanced glycosylation end products (AGEs).

Anti-glycation components are used in the topical composition to reduce glycation of collagen. Vitamin E is known to significantly reduces glycation and production of AGEs. Tocopherol is a series of organic compounds consisting of various methylated phenols, which is a class of chemical compounds of which many have vitamin E activity. Tocotrienols, with four d-isomers, also belong to the vitamin E family. Tocotrienol has been shown clinically to be 40-50 times stronger and more effective at repairing skin damage than regular Vitamin E. Tocopherols and tocotrienols are fat-soluble antioxidants, they can disperse in a cell membrane, therefore, eliminate free radicals far more efficiently than regular Vitamin E.

Tocotrienol/tocopherol complex is commercially available under the trade name of Tocomin® from CAROTECH Inc. (Edison, N.J.). Tocomin® is a series of products contain natural occurring mixture of tocotrienols and tocopherol extracted and concentrated from virgin crude palm oil/palm fruits (*Elaeis guineensis*). The Tocomin® also contain other phytonutrients such as plant squalene, phytosterols, co-enzyme Q10 and mixed carotenoids that are naturally extracted together with tocotrienols from palm fruits. Tocotrienol/tocopherol complex is used in the topical composition of the present invention in a concentration range from about 0.05% to about 0.2% (w/w) of Tocomin® (50% c).

Examples of suitable collagen stimulating components include, but are not limited to, methylsulfonylmethane, phytosterols, tetrahexyldecyl ascorbate, metallic sicates, *Pisum sativum* (pea) extract, and dimethylethanolamine, and estrogen.

Methylsulfonylmethane (MSM) is an organic source of bioavailable sulfur, which is crucial to body function and structure, found naturally in the body and in all living organisms. Methylsulfonylmethane inhibits cross linking of collagen and therefore is useful to reduce hardening of connective tissue with age. Methylsulfonylmethane has also been used in ophthalmic formulations as a skin permeation enhancer facilitating permeation of the formulation through the skin, when the formulation is applied to the eyelids. In addition, methylsulfonylmethane is required in DNA repair. Methylsulfonylmethane is used in the topical composition at a concentration in a range from about 0.1% to about 0.5% (w/w).

Phytosterols used in the topical composition are derived from vegetable oils. Naturally occurring phytosterols are usually a mixture of various sterols (e.g., campesterol, stigmasterol, among others). Structurally similar to cholesterol, phytosterols have been found to protect skins weakened by hormonal deficiencies, re-densify the dermis to remodel the skin, and smooth out structural wrinkles. The skin treated by phytosterols is visibly firmer and younger, and the depth of structural wrinkles visibly diminishes. Furthermore, it is believed that the active components of naturally occurring phytosterols retard inflammation processes.

Furthermore, a second different combination may be used, namely, a complex of silicates of sodium, magnesium and aluminum; *Pisum sativum* (pea) extract; and glucosamine hydrochloride is used in the topical composition for increasing the production of collagen, elastin and hyaluronic acid, and induces cell proliferation and differentiation. Such silicates are known sources of silica. Also, bamboo silica has been used in skin care products as a cross-linking agent, providing strength and resilience to collagen and elastin connective tissues. *Pisum sativum* (pea) extract has been found containing phenolic compounds, such as benzoic and cinnamic acids, cinnamic acid derivatives, flavone and flavonol glycoside, and to possess antioxidant properties. Glucosamine is an amino sugar and a prominent precursor in the biochemical synthesis of glycosylated proteins and lipids. Glucosamine hydrochloride is used for simulating hyaluronic acid production.

A complex of bamboo silica extract, *Pisum sativum* extract and glucosamine hydrochloride is commercially available under the trade name of Dermox SRC from Barnet Products Corporation (Englewood Cliffs, N.J.). An increased production of collagen, elastin and hyaluronic acid makes skin firmer and makes deeper wrinkles less visible. The concentration of Dermox SRC in the topical composition is in a range from about 0.5% to about 2% (w/w).

It is to be appreciated that silicates of sodium, magnesium and aluminum may be used in addition to or in lieu of bamboo silica, also known as *Bambusa vulgura*. Where said metallic silicates are used, it also desirable to include acetyl hexapeptide-8 and phenoxyethonal and, optionally, ethylhexylglycerin for enhanced suppleness of the skin and reduction of wrinkles.

Estrogen has been known to stimulate both collagen and hyaluronic acid for some time. Estrogens are a group of steroid compounds that function as the primary female sex hormone in human body. The three naturally occurring estrogens are estradiol, estriol and estrone. Phytoestrogens are a group of naturally occurring nonsteroidal plant compounds. Because of their structural similarity with estradiol (17-.beta.-estradiol), phytoestrogens have the ability to cause estrogenic effects. Suitable estrogens for the purpose of the present invention include, but are not limited to, estriol, estradiol, estrone, phytoestrogens, or combination thereof. In one embodiment, estriol is used for stimulating collagen or elastin production.

It is known that most of the hydration in the skin is dependent on hyaluronic acid levels in the intra and extracellular matrix. The more hyaluronic acid the skin contains, the more water the skin will retain. Hyaluronic acid production normally decreases with age, consequently, both the cells and the gel substance between the cells becomes less hydrated. This reduces delivery of nutrients necessary for skin regeneration and DNA repair into the cells, as well as reduces cell waste removal out of the cell. Therefore, poor metabolic pathway function can be caused by poor cell nutrition due to poor cell hydration. This leads to rapid and premature cellular aging. Cellular hydration compounds increase hyaluronic acid production. Enhancing cellular hydration provides softer looking and feeling skin, and helps to reduce wrinkle depth and new wrinkle formation.

Dimethylethanolamine is used in the topical composition as a cellular hydration compound. Dimethylethanolamine is a nutrient naturally produced in the human brain. When applied on the skin, dimethylethanolamine gives an almost immediate increase in the appearance of tone and continues to firm skin over time. Dimethylethanolamine is also an antioxidant. Dimethylethanolamine is considered as a foodgrade substance, safe to use in dermatological products. In the topical composition of the present invention, dimethylethanolamine is in a concentration range from about 0.2% to about 0.8% (w/w).

Age spot reduction components are used to treat and inhibit age dependent color changes to the skin. These compounds decrease pigment depositions and help to even skin tone. Furthermore, in terms of pigmentation, previously described DNA repair components continuously reduce, as well as inhibit, the formation of new age related pigmentations which are also known as lipofuscin deposits.

*Glycyrrhiza Glabra* (licorice) root extract is used in the topical composition of the present invention as an age spot reduction component, in a concentration range from about 0.005% to about 0.03% (w/w). *Glycyrrhiza Glabra* (licorice) root extract contains active component of glabridin. Glabridin has a strong tyrosinase-inhibition activity, which is 25 times higher than Kojic acid and 75 times higher than ascorbic acid. Glabridin is also an antioxidant and has UV absorbing property.

*Glycyrrhiza Glabra* (licorice) root extract is commercially available under the trade name of Licorice P-TH from Barnet Products Corporation (Englewood Cliffs, N.J.). In vivo study has shown that at a concentration of 0.05% of Licorice P-TH, the extract effectively decreases post-inflammatory hyperpigmentation in more than 80% of the individuals tested. In the topical composition of the present invention, *Glycyrrhiza Glabra* (licorice) root extract is used in a concentration range from about 0.005% to about 0.03% (w/w).

Additionally, the water soluble extract of the *Uncaria* species described above is also believed to function as a bleaching agent.

In one embodiment, the topical composition comprises water soluble extract of *Uncaria* species, *Arabidopsis thaliana* extract, lipoic acid, dimethylethanolamine, tetrahexyldecyl ascorbate, dimethyl sulfoxide, *Glycyrrhiza Glabra* (licorice) root extract, methylsulfonylmethane, phytosterols, d-ribose, tocopherol, *Pisum sativum* extract, glucosamine hydrochloride, and a dermatological acceptable liposomal delivery medium.

As described above, one major feature of the topical composition of the present invention is its dual actions in DNA repair in both the nucleus and the mitochondria. To achieve an effective DNA repair in the nucleus and in the mitochondria, the active components need to be delivered through the cellular membrane to the target areas. To accomplish this, a liposomal delivery system or medium is used in the topical composition to encapsulate the active components and to enhance their penetration through the epidermis and then to enter the dermis layer. Liposomes can penetrate through cellular membrane and deliver the active components to the inside of cells. Other delivery vehicles, such as nosome or rivosome, can also be used in the topical composition.

The medium further comprises solvents, emulsifiers, emollients, binders, and moisturizers known in the art. In one exemplary embodiment, the medium of the topical composition comprises water, butylene glycol, propylene glycol, glyceryl stearate, PEG-100 stearate, *brassicca campestris/aleurites fordi* oil copolymer, cyclopentasiloxane and dimethicone/vinyl dimethlcone crosspolymer, cyclopentasiloxane, C12-15 alkyl octonoate, cetyl alcohol, bis-diglyceryl polyacyladipate-2, lecithin, maltodextrin, sorbitan stearate, ethylene/acrylic acid copolymer, titanium dioxide, methyl glucose sesquistearate, PEG-20 methyl glucose sesquistearate, acrylates/C10-30 alkyl acrylate crosspolymer, sodium silicate, magnesium aluminum silicate, acetyl hexapeptide-8, polyoxyethanol, and *butyrospermum parkii* (shea butter).

The topical composition may further comprise one or more preservatives, such as phenoxyethanol, methylparaben, ethylparaben, butylparaben, triethanolamine, and tetrasodium EDTA. These chemicals have antimicrobial activities for preserving the product. The concentration of the preservatives is sufficient to inhibit microbial growth, without causing skin irritation or interference of the active components described above. Optionally, the topical composition may also comprise a fragrance and coloring agents such as Yellow 5 and Red 40.

The topical composition of the present invention can be provided in a variety of forms such as lotion, cream, spray, gel, and aqueous suspension.

In a further aspect, the present invention provides a method of anti-aging skin treatment. In one embodiment, the method comprises topically applying an effective amount of the topical composition of the present invention on one or more areas of the skin of a person. The area may include, but not limited to, forehead, eye area, perioral area, cheek, the entire face, neck, chest or hands. In one embodiment, the topical composition is topically applied on the areas one or more times daily. Typically, the skin area is covered by a thin layer of the topical composition.

In one study among 59 women between age 30 and 60, after applying the cream set forth herein once daily in the night for a period of from one month to twelve months, more than 80% of the subjects achieved noticeable improvements in reduction of the degree of wrinkles, and more than 85% of the subjects achieved noticeable improvements in the skin color tone. The improvements were observed in the forehead, crows feet and eye area, perioral area, and the face in general. A quantitative evaluation of the pigmentation spots on the face of the subjects using Digital Visia Complexion Analysis showed an average reduction of the feature count of the spots from 33.15% to 56.25% upon completion of the treatment.

Figure 2:
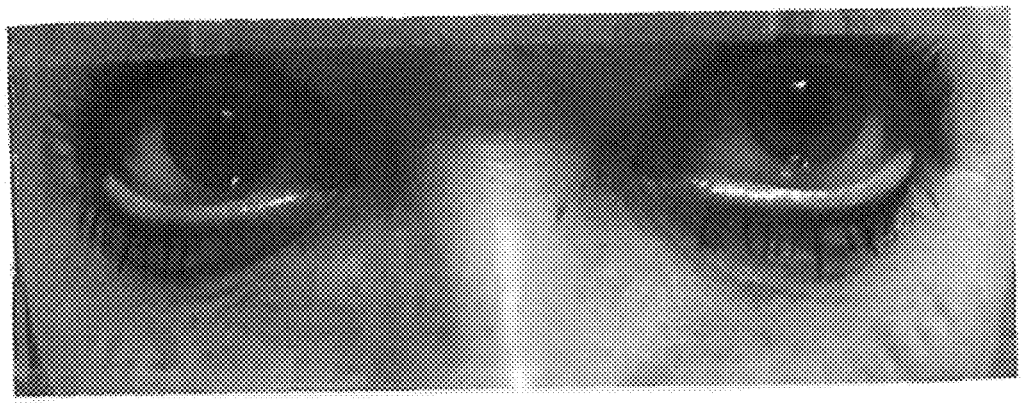
FIGS. 2, 4 and 6 are photographs of the same subjects after about two months of use of the composition.
Figure 3:
Figure 4:
Figure 5:
Figure 6:
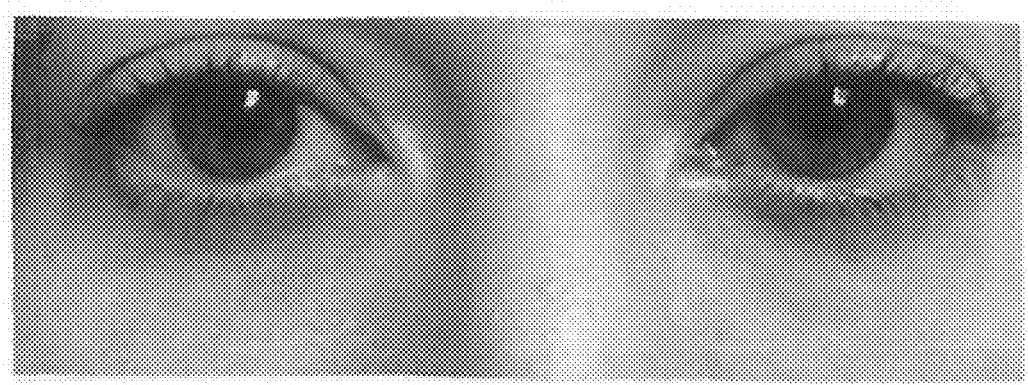

Shown in FIGS. 1, 3 and 5 are photographs of the eye area of three of the above subjects prior to treatment with the inventive composition. FIGS. 2, 4, and 6 show changes in appearance of the same three subjects after two months of use. As may be seen, the results of the therapy are most noticeable.

In another study, the topical composition was used in a skin infusion or dermal infusion treatment. Dermal infusion is a procedure that provides noninvasive exfoliation and delivers a topical solution under pressure to treat dermatological conditions. It has been used to treat rosacea, dehydration, acne, and post-inflammatory hyperpigmentation. In one embodiment, the topical composition of the present invention, in the form of an aqueous suspension, can be filled into a known dermal infusion device and then applied to the skin. The topical composition may be applied with or without micro-dermal abrasion or skin suction, as well as applied topically to the skin in a separate dual compartment syringe applicator where the different mixtures of the dual DNA repair compound and the skin tightening compound are kept separated until they exit the applicator device and mixed together at the time of use.

All publications, patent applications, patents, and other references mentioned herein are incorporated by reference in their entirety.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

We claim:

1. A method of reducing pigmentation spots, treating wrinkles and improving skin color tone of skin in a person in need thereof comprising topically applying to one or more areas of the skin, an effective amount of a composition comprising as active agents:
   (a) *arabidopsis thaliana* extract in a concentration range from about 0.5% to about 2% (w/w);
   (b) a water soluble extract of *Uncaria* species in a concentration range from about 0.5% to about 5% (w/w);
   (c) alpha lipoic acid in a concentration range from about 1% to about 5% (w/w);
   (d) dimethylethanolamine in a concentration range from about 0.2 to about 0.8% (w/w);
   (e) tetrahexyldecyl ascorbate in a concentration range from about 0.5% to about 2% (w/w);
   (f) dimethyl sulfoxide in a concentration range from about 0.5% to about 2% (w/w);
   (g) *glycyrrhiza glabra* (licorice) root extract in a concentration range from about 0.005% to about 0.3% (w/w);
   (h) methylsulfonylmethane in a concentration range from about 0.1 to about 0.5% (w/w);
   (i) phytosterols in a concentration range from about 0.1 to about 0.6% (w/w);
   (j) D-ribose in a concentration range from about 0.01 to about 0.05% (w/w);
   (k) a mixture of tocopherol and phytonutrients in an a concentration range of from about 0.5% to about 2% (w/w), wherein the phytonutrients are plant squalene, phyotsterols, co-enzyme Q10 and mixed carotenoids;
   (l) a complex of silicates of sodium, magnesium and aluminum, *Pisum sativum* extract and glucosamine hydrochloride in an amount of from about 1.0% to about 10% (w/w);
   (m) a medium for delivering liposomes; and (n) preservatives; and wherein the composition provides DNA repair of the nucleus and mitrocondria.

2. The method of claim 1, in which said complex including silicates comprising:
   sodium silicate and magnesium aluminum silicate.

3. The method of claim 2, further comprising: acetyl hexapeptide-8.

4. The method of claim 3, further including:
   phenoxyethanol and ethylhexylglycerin.

5. The method of claim 3, further comprising:
   *Bambusa vulgris* extract.

6. The method of claim 5, wherein said topical composition is topically applied to the one or more areas of skin one or more times daily.

7. The method of claim 5, wherein said topical composition further comprises estriol.

8. The method of claim 5, wherein the one or more areas of skin are on the forehead, eye area, perioral area, cheek, face, neck, chest or hands, or body.

9. The method of claim 7, wherein said topical composition is topically applied on the one or more areas of skin with dermal infusion.

10. The method of claim 9, wherein the dermal infusion is micro-dermal abrasion or skin suction.

* * * * *